(12) United States Patent
Gerrans

(10) Patent No.: US 10,588,502 B2
(45) Date of Patent: Mar. 17, 2020

(54) SIDE LOADING ARTICULATING LARYNGEAL ACCESS SYSTEM

(71) Applicant: Sanovas Intellectual Property, LLC, Reno, NV (US)

(72) Inventor: Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 424 days.

(21) Appl. No.: 15/355,690

(22) Filed: Nov. 18, 2016

(65) Prior Publication Data

US 2017/0135566 A1 May 18, 2017

Related U.S. Application Data

(60) Provisional application No. 62/256,744, filed on Nov. 18, 2015.

(51) Int. Cl.
| | |
|---|---|
| *A61B 1/267* | (2006.01) |
| *A61B 5/00* | (2006.01) |
| *A61B 1/06* | (2006.01) |
| *A61B 1/005* | (2006.01) |
| *A61B 1/05* | (2006.01) |

(Continued)

(52) U.S. Cl.
CPC ............ *A61B 1/267* (2013.01); *A61B 1/0052* (2013.01); *A61B 1/0055* (2013.01); *A61B 1/0056* (2013.01); *A61B 1/0057* (2013.01); *A61B 1/00082* (2013.01); *A61B 1/012* (2013.01); *A61B 1/04* (2013.01); *A61B 1/05* (2013.01); *A61B 1/0607* (2013.01); *A61B 1/0676* (2013.01); *A61B 1/0684* (2013.01); *A61B 5/14551* (2013.01); *A61B 5/6847* (2013.01);

(Continued)

(58) Field of Classification Search
CPC ......... A61B 1/267; A61B 1/0607; A61B 1/05; A61B 1/0057; A61B 1/0676; A61B 1/012
See application file for complete search history.

(56) References Cited

U.S. PATENT DOCUMENTS

| | | |
|---|---|---|
| 3,081,767 A | 3/1963 | Hett |
| 3,565,079 A | 2/1971 | Jackson |

(Continued)

OTHER PUBLICATIONS

Takashi Asai, M.D., Ph.D, et al., "Use of the Pentax-AWS® in 293 Patients with Difficult Airways", Anesthesiology 2009; 110: pp. 898-904. Copyright © 2009, the American Society of Anesthesiologists, Inc. Lippincott Williams & Wilkins, Inc.

*Primary Examiner* — Bradley J Osinski
(74) *Attorney, Agent, or Firm* — Forge IP, PLLC

(57) ABSTRACT

A laryngeal access system includes a laryngeal blade with a proximal portion and a distal portion, an inner channel extending longitudinally through the laryngeal blade, wherein an outer wall of the laryngeal blade has an opening therethrough extending from the proximal portion to the distal portion of the blade through which an object can pass through the outer wall into the inner channel, an articulating member provided at the distal portion of the blade, and an actuator provided at the proximal portion of the blade and coupled to the articulating member, wherein the actuator moves the articulating member from a first position, in which the articulating member has a first longitudinal axis, to a second position, in which the articulating member extends at an angle relative to the first longitudinal axis.

17 Claims, 8 Drawing Sheets

(51) Int. Cl.
*A61B 1/00* (2006.01)
*A61B 1/012* (2006.01)
*A61B 1/04* (2006.01)
*A61B 5/1455* (2006.01)
*A61B 5/0205* (2006.01)
*A61B 5/021* (2006.01)
*A61B 5/024* (2006.01)

(52) U.S. Cl.
CPC ............... *A61B 5/021* (2013.01); *A61B 5/024* (2013.01); *A61B 5/02055* (2013.01)

(56) References Cited

U.S. PATENT DOCUMENTS

| | | | |
|---|---|---|---|
| 4,114,626 A * | 9/1978 | Beran | A61M 25/02 128/DIG. 26 |
| 4,817,598 A * | 4/1989 | LaBombard | A61M 16/0465 128/207.14 |
| 5,643,221 A | 7/1997 | Bullard | |
| 5,763,792 A * | 6/1998 | Kullik | A61B 5/087 600/538 |
| 6,142,144 A | 11/2000 | Pacey | |
| 6,174,281 B1 * | 1/2001 | Abramowitz | A61B 1/2673 600/196 |
| 8,366,612 B2 | 2/2013 | Rosenthal | |
| 8,457,715 B2 | 6/2013 | McKenna et al. | |
| 8,457,716 B2 | 6/2013 | Li et al. | |
| 8,812,081 B2 | 8/2014 | Li et al. | |
| 8,864,657 B2 | 10/2014 | Tydlaska | |
| 8,886,290 B2 | 11/2014 | Li et al. | |
| 8,998,798 B2 | 4/2015 | Hayman et al. | |
| 2010/0145146 A1 | 6/2010 | Melder | |
| 2010/0179511 A1 * | 7/2010 | Rajan | A61M 11/00 604/514 |
| 2011/0196204 A1 * | 8/2011 | Setty | A61B 1/00052 600/120 |
| 2012/0078055 A1 | 3/2012 | Berci et al. | |
| 2014/0275778 A1 * | 9/2014 | Gunday | A61M 16/0488 600/109 |

* cited by examiner

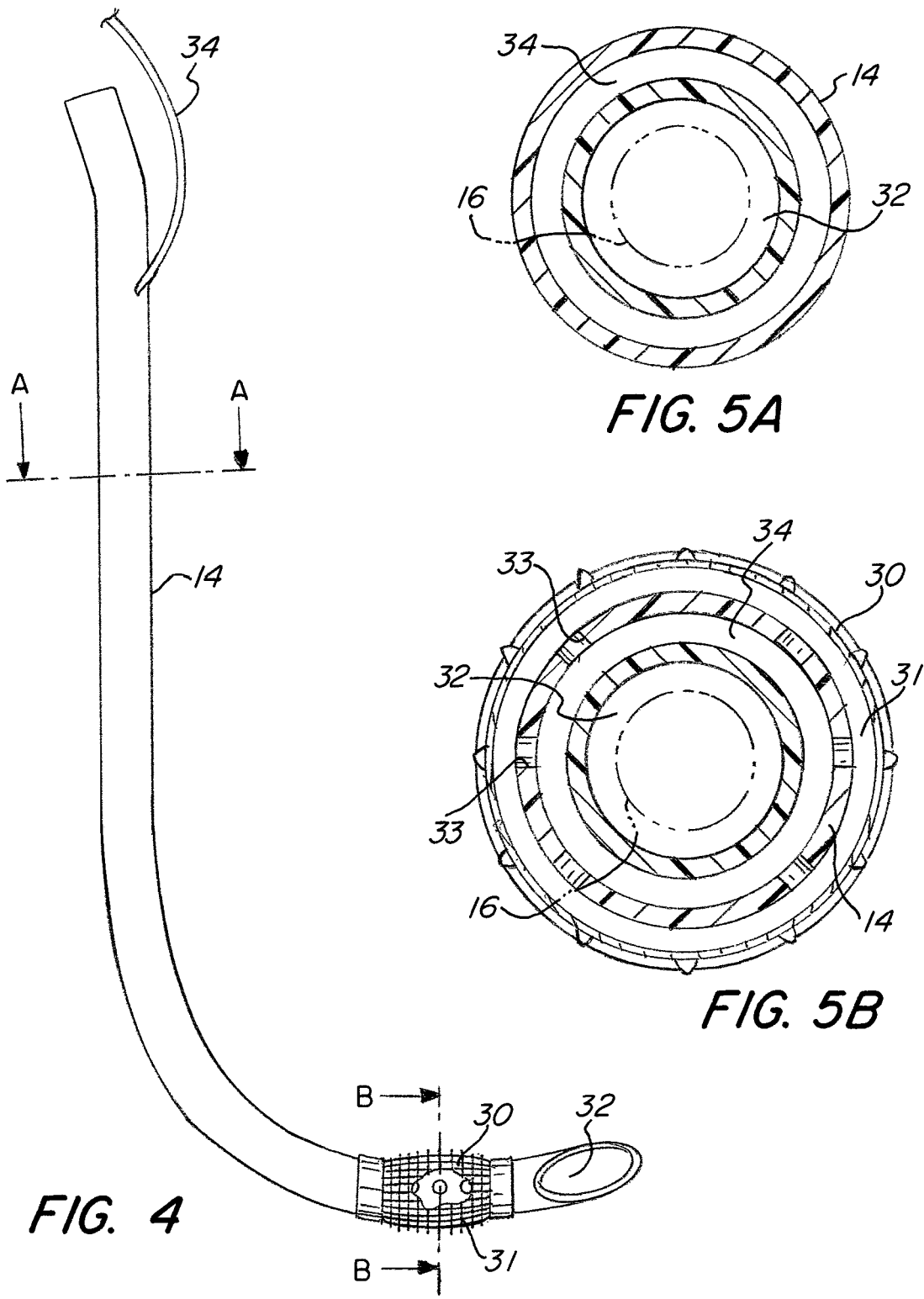

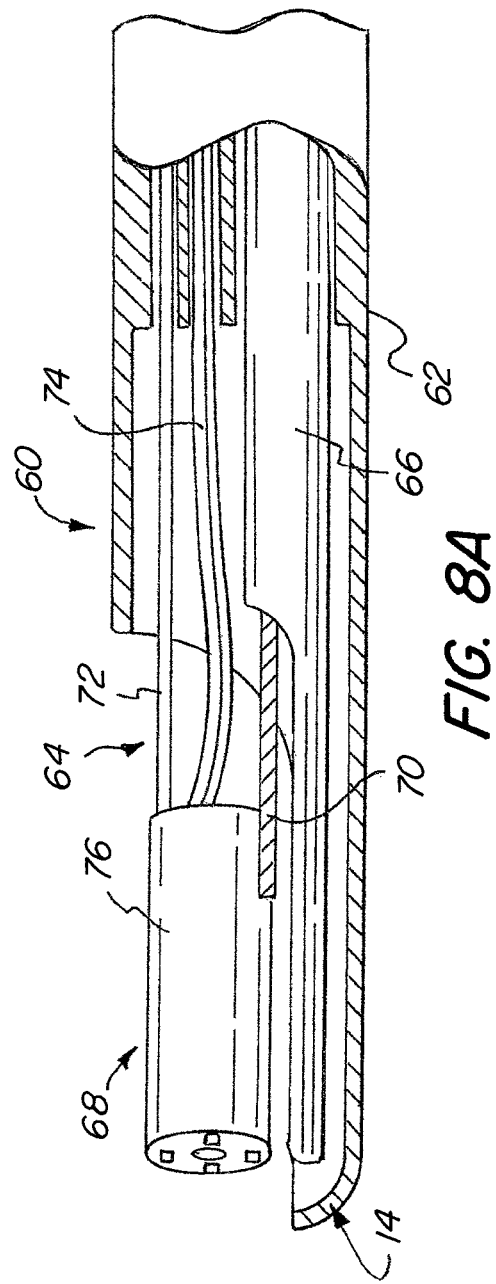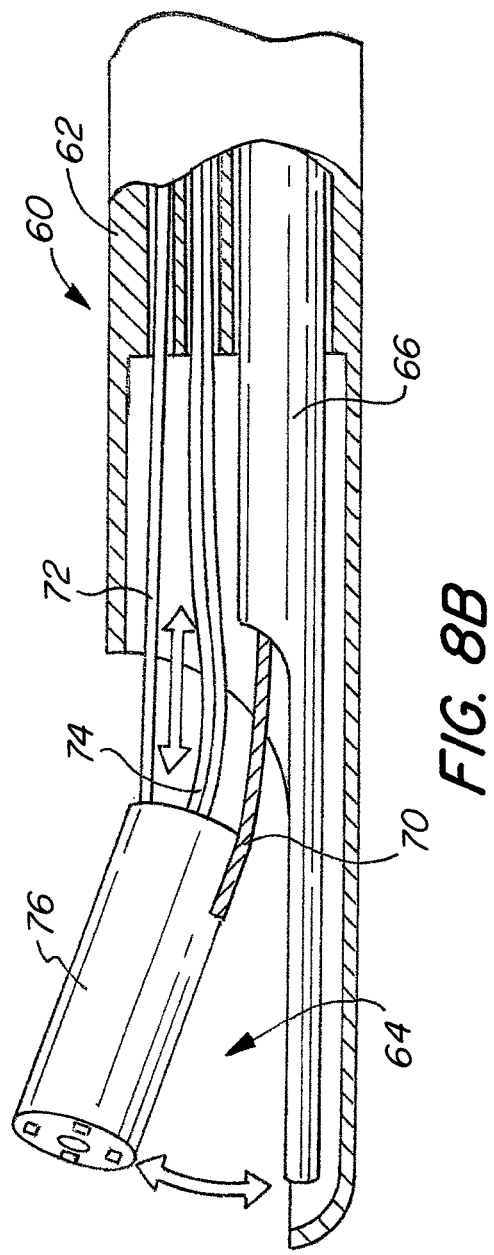
FIG. 8A
FIG. 8B

SIDE LOADING ARTICULATING LARYNGEAL ACCESS SYSTEM

FIELD OF THE INVENTION

The invention relates to a medical intubation device, and more specifically, to a side loading articulating laryngeal access system for performing intubation procedures.

BACKGROUND OF THE INVENTION

In critically injured, ill or anesthetized patients, it is often necessary to insert an endotracheal tube into a person's airway to facilitate ventilation of the lungs and to prevent the possibility of asphyxiation or airway obstruction. The most common routes of inserting the endotracheal tube are oral, in which the tube is passed through the mouth and larynx into the trachea, and nasal, wherein the tube is passed through the nose and larynx into the trachea.

The insertion of the endotracheal tube often involves serious risks, such as damage to the vocal cords and a prolonged intubation procedure in which the patients breathing is stopped, but oxygen is not yet delivered to the patient as the tube has not yet been inserted. It is estimated that about one third of deaths occurring during a surgical procedure while under anesthesia for morbidly obese patients are associated with the intubation process. Some of the difficulties that persons performing endotracheal intubation encounter include the restriction of view as the tube is inserted, variations in the anatomy of the patients, an uncomfortable and unnatural position of the person performing the procedure while holding the instrument, and the necessity for rapid intubation.

With the advent of various video devices and cameras, instrumentation has been improved to the extent that it can enable viewing of the cords and larynx on a video screen thereby facilitating the intubation of the patient in a relatively quick and safe manner. However, the known imaging intubation devices still suffer from a number of disadvantages and drawbacks.

For example, with the current systems, the intubation is typically accomplished by inserting a rigid laryngeal blade into a person's trachea, and then inserting an endotracheal tube alongside the blade. Such rigid laryngeal blades are pre-shaped to have a certain curvature generally corresponding to the curvature of a person's airway passage anatomy. However, different types of patients often have different anatomies and it may be challenging to use the rigid blade for different types of patients because the blade's shape cannot be easily adjusted to fit the anatomy of a particular patient, particularly at the distal end of the blade.

Additionally, because the current systems require separate insertion of the laryngeal blade and the endotracheal tube, they require significant time to set up and to insert into the patient. In emergent situations this delay could be hazardous, if not deadly.

Another major problem with current systems is the limited field of view, requiring more time for the user to intubate the patient. Typically, the imaging device is positioned at a distal tip of the device body which only provides a limited view of the surrounding tissue, even if the distal tip is capable of being angled to a certain degree.

What is desired, therefore, is an improved system and method for intubating a patient that address the disadvantages and shortcoming of the prior art systems described above.

SUMMARY OF THE INVENTION

It is therefore desired to provide an improved laryngeal access system that can be easily adjusted to fit anatomy of different types of patients.

It is further desired to provide an improved laryngeal access system with components that can be quickly and easily assembled to facilitate emergent intubation of a patient.

It is also desired to provide an improved laryngeal access system that provides the user with a greater field of view to facilitate a quicker intubation and reduce the probably of injuring the patient.

It is yet further desired to provide an improved laryngeal access system that provides enhanced and more efficient user control during the intubation process.

In order to achieve at least the above-mentioned objects of the present invention, a laryngeal access system is provided including a laryngeal blade with a proximal portion and a distal portion, an inner channel extending longitudinally through the laryngeal blade, wherein an outer wall of the laryngeal blade has an opening therethrough extending from the proximal portion to the distal portion of the blade through which an object can pass through the outer wall into the inner channel, an articulating member provided at the distal portion of the blade, and an actuator provided at the proximal portion of the blade and coupled to the articulating member, wherein the actuator moves the articulating member from a first position, in which the articulating member has a first longitudinal axis, to a second position, in which the articulating member extends at an angle relative to the first longitudinal axis.

In certain embodiments, an inner wall of the blade has at least one protrusion extending into the channel and configured to movably grip an object positioned in the inner channel.

In some embodiments, the actuator moves the articulating member from the first position to the second position in response to application of pressure thereto by a user's hand.

In certain embodiments, the actuator is activated by a linear displacement of the actuator by a user's finger. In additional embodiments, the actuator is activated by a rotational movement of the actuator by a user's finger.

In some embodiments, the actuator is coupled to the articulating member via a wire.

In certain embodiments, the system further includes an imaging device movably disposed in the inner channel. In some of these embodiments, the imaging device includes at least one of a CMOS device and a CCD device. In additional embodiments, the imaging device includes at least one illumination device generating light for illuminating surrounding tissue.

In some embodiments, a portion of the laryngeal blade proximal to the distal end of the blade is substantially flexible such that it bends when the articulating member is moved to a second position.

In certain embodiments, at least a portion of the laryngeal blade is substantially transparent to allow for imaging of surrounding tissue through the blade.

In some embodiments, the articulating member comprises an imaging device disposed thereon. In certain of these embodiments, the articulating member further includes an illumination device positioned adjacent the imaging device.

In certain embodiments, the laryngeal blade includes at least one sensor positioned thereon. In some of these embodiments, the at least one sensor includes at least one of a pulse oximetry sensor, a blood pressure sensor, a temperature sensor, a flow sensor and a biofilm sensor.

In some embodiments, the laryngeal access system further includes an endotracheal tube removably accommodated in the inner channel via the opening and having a lumen. In certain of these embodiments, the endotracheal tube includes an inflatable balloon positioned adjacent a distal end of the endotracheal tube.

In certain embodiments, the laryngeal system further includes a fluid source coupled to the inflatable balloon via an inflation lumen provided in the endotracheal tube.

Other objects of the invention and its particular features and advantages will become more apparent from consideration of the following drawings and accompanying detailed description.

BRIEF DESCRIPTION OF THE DRAWINGS

FIG. 4 is a partially cross-sectional front perspective view of an endotracheal tube of the laryngeal access system of FIG. 1A.

FIGS. 5A and 5B are cross-sectional views of the endotracheal tube of FIG. 4 taken along the lines "A-A" and "B-B" respectively.

FIGS. 8A and 8B are partially cross-sectional view of an imaging stylet used with the laryngeal access system of FIG. 1A.

DETAILED DESCRIPTION OF THE INVENTION

Figure 1A:
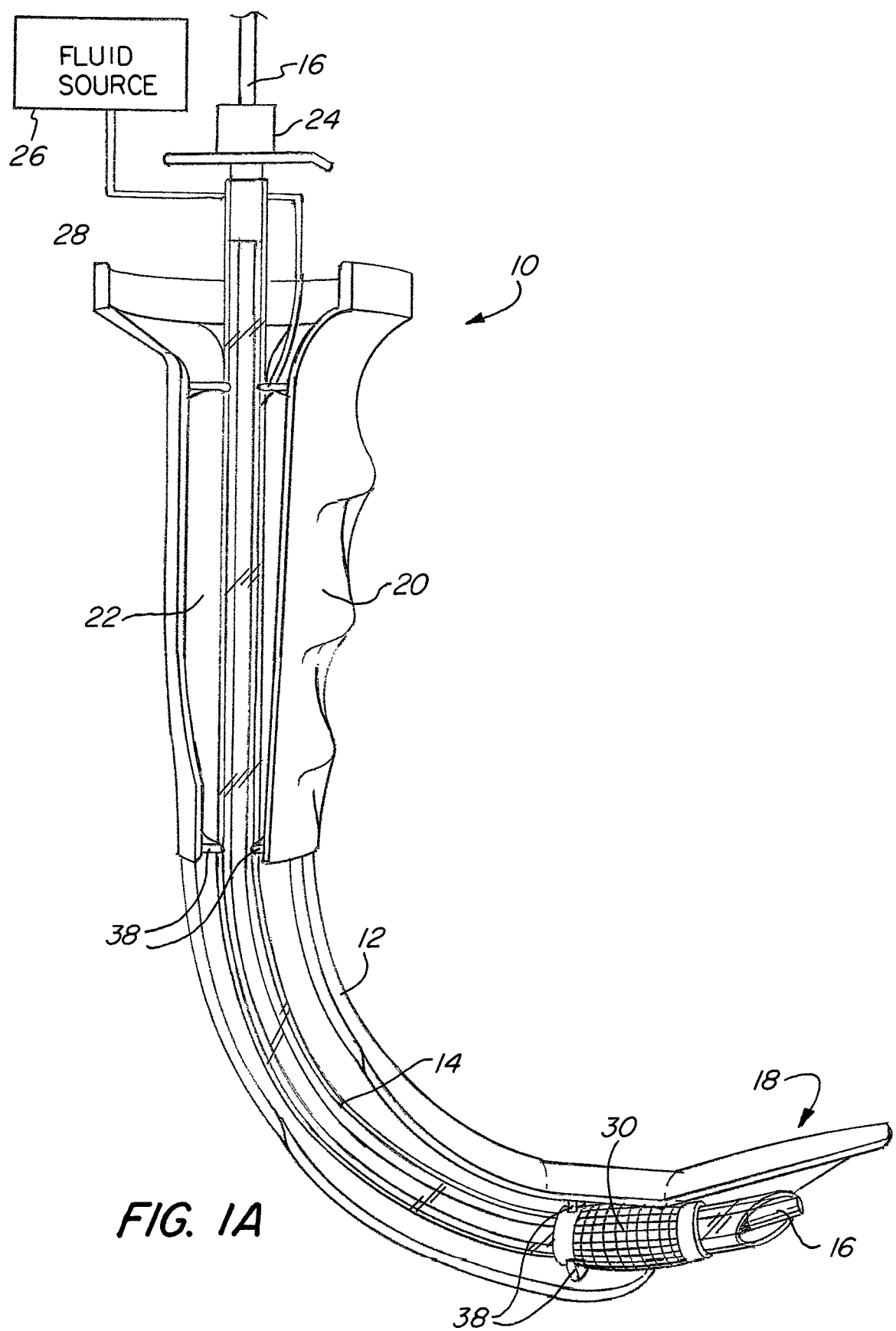
FIG. 1A is a front perspective view of the laryngeal access system in accordance with the present invention.

The basic components of one embodiment of a laryngeal access system in accordance with the invention are illustrated in FIG. 1A. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1A, the laryngeal access system (10) includes a laryngeal blade or cannula (12). In some embodiments, the blade (12) is made with any suitable rigid or semi-rigid material, such as, e.g., metal or polymer, and is pre-shaped to correspond to the anatomy of a person's throat and trachea. In other embodiments, the blade (12) may be made with malleable material, such that the blade can be bent into a desired shape right before the intubation procedure to more precisely correspond to the anatomy of the patient undergoing intubation. For example, children's trachea anatomy differs from that of an adult and the shape of the laryngeal blade may need to be adjusted to accommodate intubation of pediatric patients.

The blade (12) has a hollow interior connected to a distal end opening and a proximal end opening. The hollow interior accommodates various instruments and devices necessary for the intubation procedure, such as an endotracheal tube and an imaging device, as described in more detail below.

The laryngeal blade (12) also includes an articulating member (18) positioned above the distal end opening, as shown in FIG. 1A. The articulating member (18) is capable of articulating to different angles of deflection in all directions, as well as performing rotational articulation. The articulation of the member (18) assists a physician performing an intubation in safely and efficiently accessing the subject's trachea anatomy to deflect various structures, e.g., the subject's tongue, to position the blade inside the subject's trachea.

The articulation of the member (18) is performed via an actuator positioned at the proximal end of the blade (12) and coupled to the articulating member (18). Various suitable actuator types may be used in accordance with the present invention. In the embodiment illustrated in FIG. 1A, the actuator is pressure based. In other words, the physician performing the intubation procedure applies pressure to a hand grip (20) provided at the proximal end of the blade (12) by squeezing the hand grip. The application of pressure translates to the articulation of the member (18) of the blade.

Figure 1B:
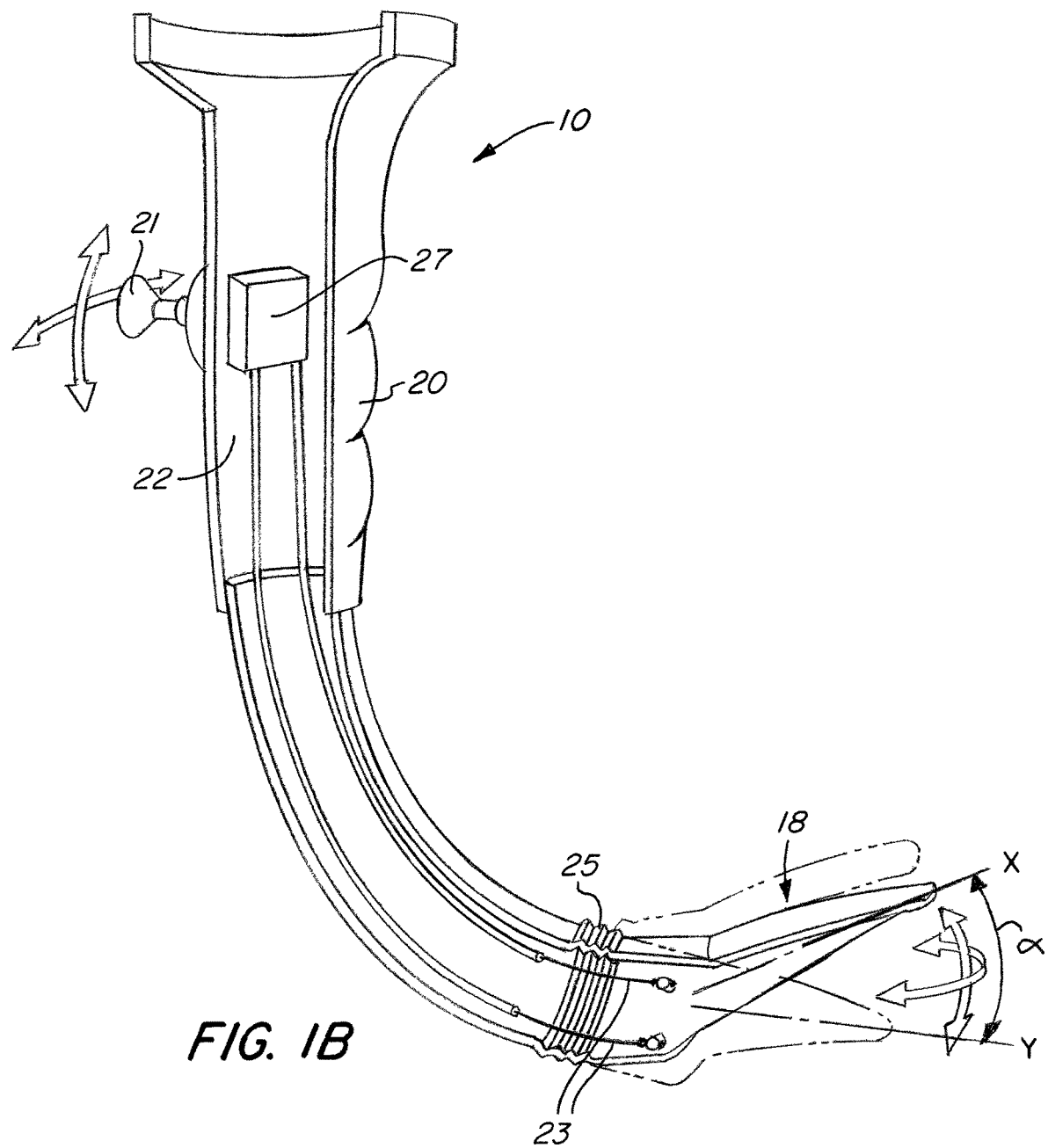
FIG. 1B is a front perspective view of another embodiment of the laryngeal access system in accordance with the present invention.
Figure 2:
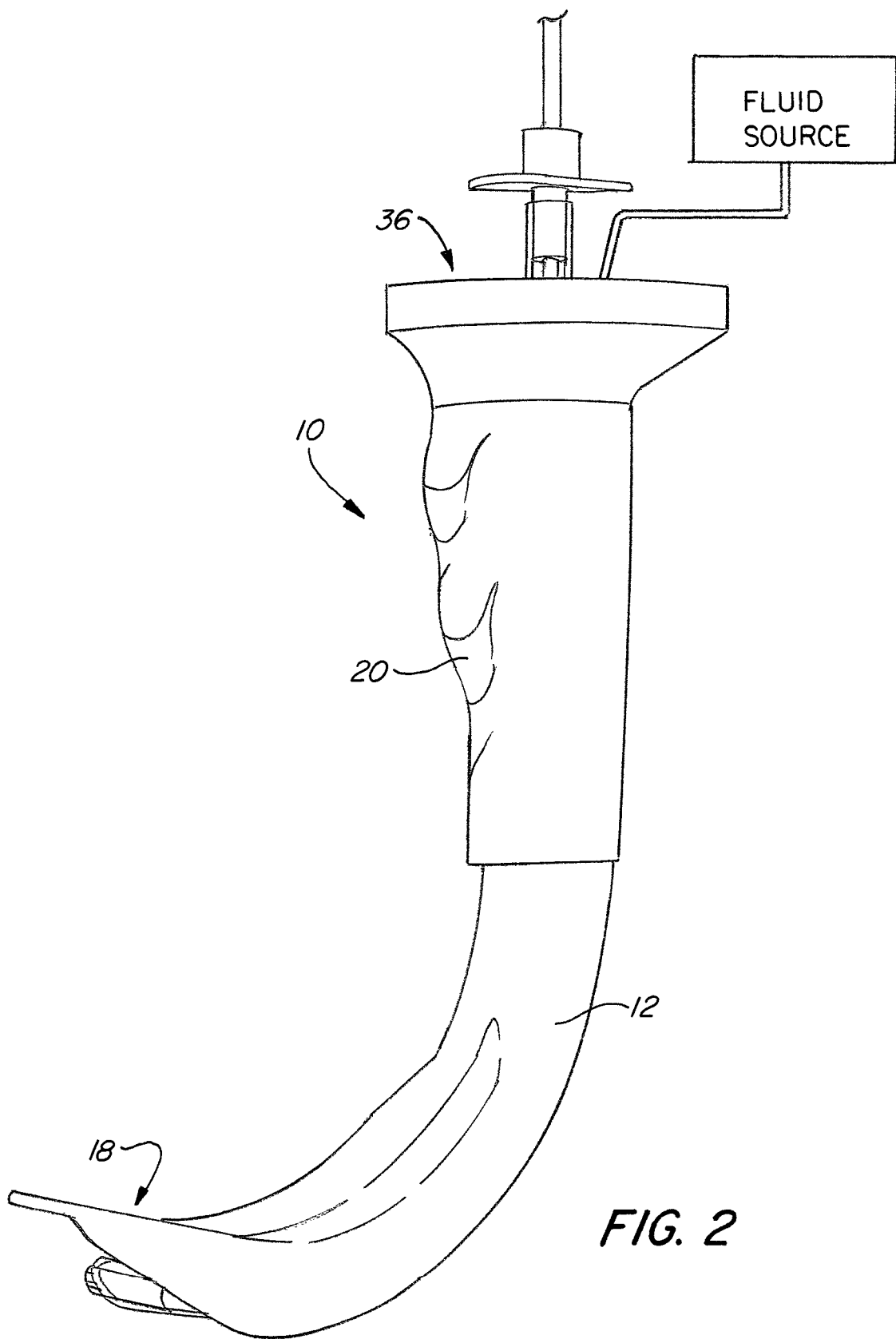
FIG. 2 is a rear perspective view of the laryngeal access system of FIG. 1A.

In other embodiments, such as shown in FIG. 1B, the member (18) is articulated by a linear, e.g., horizontal, vertical or diagonal, or rotational displacement of the actuator by the physician's finger. The actuator is in the form of a button or a joystick (21) provided on the outer surface of the proximal portion of the blade opposite the hand grip (22). This positioning makes it convenient for the physician to use his or her thumb to actuate the button (21). It is understood that in other embodiments, the actuator (21) may be provided on the hand grip portion (22) or at any other convenient location on the proximal portion of the blade (12).

In additional embodiments, the actuator may be in the form of a handle with a pistol-type grip and a trigger-type lever having a closed loop into which a user may insert a finger. In further embodiments, the actuator may be a button that slides in a channel provided in the wall of the proximal portion of the blade (12). The linear displacement of the button within the channel is transmitted to the articulating member (18) via any mechanisms described below to deflect the member (18).

The actuator (21) is coupled to one or more wires (23) that connect the actuator with the articulating member (18) to enable movement of the member (18). The wires (23) are connected to the actuator (21) through a transmission box (27) that translates movement of the actuator by the use into movement of the wires and the articulating member (18). In additional embodiments, piezoelectric or pneumatic mechanism or a tensioning skin may be used in place of the wires (23) to enable actuation of the articulating member (18). The actuator (21) moves the articulating member (18) from a first position in which the member (18) has a first longitudinal axis X to a second position, in which the member (18) has a second longitudinal axis Y that is angularly offset from the first axis X at an angle alpha ($\alpha$).

The articulating member (18) is coupled to the blade (12) via any suitable connection that allows for deflection of the member (18). In some embodiments, a flexible collar (25) connects the articulating member (18) to the distal portion of the blade (12). In additional embodiments, the section of the blade (12) proximal to the articulating member (18) is sufficiently flexible such that it will also bend to a degree when the member (18) is articulated.

The laryngeal blade (12) further includes a side-loading channel (22) extending along the blade, as illustrated in FIG. 1. The channel (22) has an opening on one side that extends longitudinally along a length of the channel (22). The channel (22) is designed to receive various instruments, i.e., an endotracheal tube and/or an imaging device, to be positioned inside the blade (12). The side-loading channel (22) allows for one-hand use of the system (10) during the intubation procedure. Additionally, this design allows for the endotracheal tube and/or the imaging device to be inserted into the subject's throat and trachea inside the blade (12) as opposed to the traditional side-by-side insertion, which requires more space and can be more complicated and traumatic to the patient.

The side loading channel (22) includes one or more pairs of corresponding protrusions (38). The protrusions (38) assist in maintaining an endotracheal tube and/or the imaging device in a fixed or stabilized position inside the channel (22). The protrusions (38) may be positioned at any desired location within the channel (22). It is understood, however, that the protrusions (38) still allow for linear (back and forth) displacement of the endotracheal tube and/or imaging device inside the side channel (22) of the blade (12). The protrusions (38) are made with any material that has a suitable coefficient of friction that allows for fixation and relative movement of the endotracheal tube/imaging device inside the blade (12).

Figure 3:
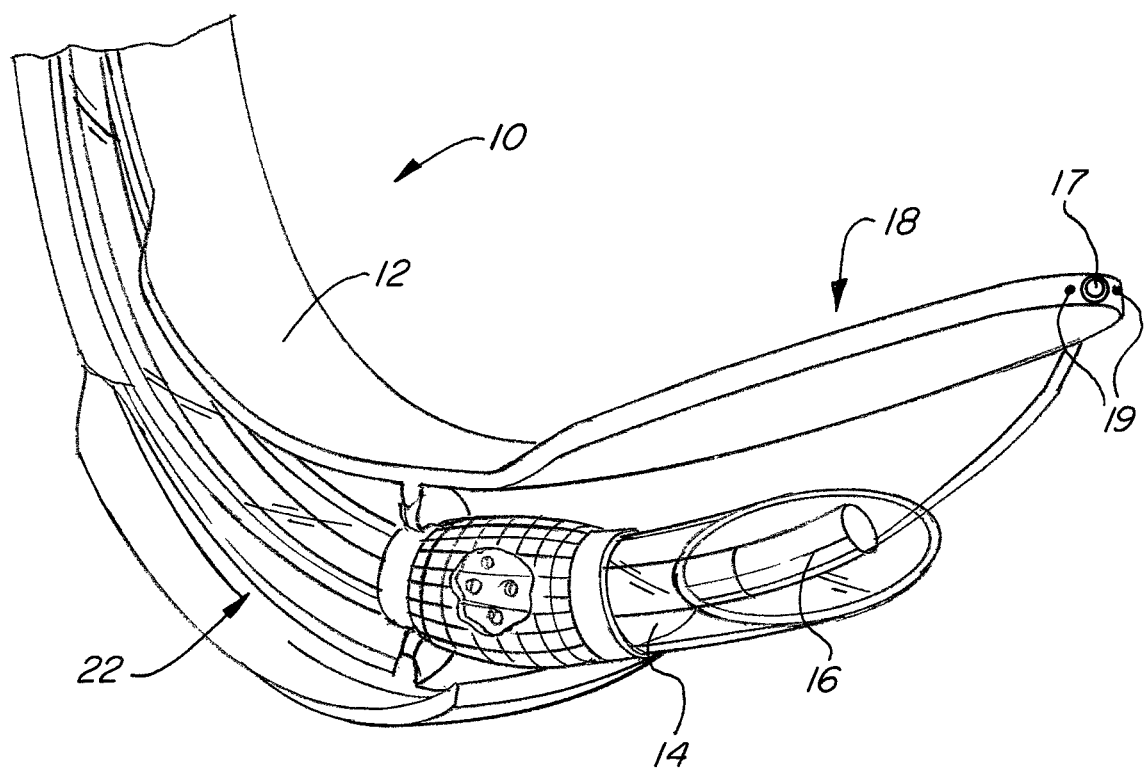
FIG. 3 is an enlarged partially cross-sectional front perspective view of a distal portion of the laryngeal access system of FIG. 1A.

In some embodiments, as shown in FIG. 3, the laryngeal blade (12) includes an imaging device (17) positioned on the articulating member (18). Any suitable known imaging device may be used in accordance with the invention. The imaging device (17) assists the physician performing the intubation procedure in imaging a patient's anatomy for faster and less traumatic intubation. The imaging device (17) may be moved to different angles by articulating the member (18) to provide different angles of view of the patient's anatomy. In additional embodiments, the laryngeal blade (12) further includes one or more sources of illumination (19), such as LEDs or optical fibers, for illumination of tracheal anatomy during the intubation procedure. The illumination devices (19) may be used with or without the imaging device (17).

In some embodiments, the laryngeal blade (12) includes one or more sensors positioned thereon. The sensors are positioned at the distal portion of the blade or in any other desirable location along the blade. The sensors may include a pulse oximetry sensor, a blood pressure sensor, a temperature sensor, a flow sensor and/or a biofilm sensor. The sensors provide various information to the physician that may be useful during and after the intubation procedure. For example, it may be desirable to measure oxygen saturation in the patient's body, or measure the patient's body temperature without having to use a separate device to obtain the measurement.

The system (10) also includes an endotracheal tube ("ET tube") (14). The ET tube (14) is inserted into a subject's trachea to establish and maintain a patent airway and to ensure an adequate exchange of oxygen and carbon dioxide. The ET tube (14) is made with any suitable material that is flexible enough to conform to the person's tracheal anatomy. The tube includes an opening at its distal end for allowing air to flow through an inner lumen (32) of the tube and also to allow for insertion of various instruments through the tube, e.g., an imaging device, to facilitate the intubation procedure.

One exemplary embodiment of the ET tube (14) is illustrated in FIGS. 4 and 5A-5B. As shown in FIG. 4, the ET tube (14) includes an inflatable balloon (30) positioned adjacent the distal end opening. In this embodiment, the ET tube (14) includes an inflation lumen (34) for supplying inflation fluid to the balloon (30) from a fluid source (26), which is shown in FIG. 1. Any suitable fluid source may be used, such as a hand-held pump or an electromagnetic pump to supply fluid to the inflatable balloon (30). It is also contemplated that, in alternative embodiments, the fluid source may be an integral part of the ET tube (14). The inflation lumen (34) is provided with any suitable connector, such as a luer connector, for connection to the fluid source (26).

As shown in FIGS. 5A and 5B, the inflation lumen (34) is separate from the inner lumen (32). This allows for inflation of the balloon (30) without compromising the passage of air through the inner lumen (32) to patient's lungs. The inflation lumen (34) may be positioned around the inner lumen (32), as shown in these figures. In other embodiments, the inner lumen (32) and the inflation lumen (34) may be positioned side by side in the ET tube (12).

The fluid source supplies a fluid, such as a gas, liquid, or mixture thereof, to the inflatable balloon (30) to inflate it. The inflation lumen (34) has one or more openings (33) positioned inside the balloon (30) to allow flow of inflation fluid to the balloon from the fluid source (26). The fluid source, i.e. a pump, may also include a variety of capabilities for balloon identification, proper inflation/deflation of the balloon, and feedback measurements, many details of which are described in U.S. Pat. No. 8,226,601 to Gunday et al. In certain advantageous embodiments, the fluid source (26) further includes a vacuum source to evacuate fluid from the balloon (30) to assist in faster deflation of the balloon.

The inflatable balloon (30) may be made of latex, Yulex, polyethylene, nylon or other suitable material, and may come in a variety of sizes and diameters, depending on a particular type of patient being intubated. The balloon (30) is attached to the outer wall of the ET tube (14) at its distal and proximal ends via any suitable method, such as via an adhesive.

In some embodiments, the balloon (30) has a wall with a textured outer surface that provides a gripping surface to facilitate anchoring the balloon (30) on the patient's airway passage. The textured outer surface of the balloon (30) may be formed by a fiber mesh affixed to the surface of the balloon during the molding process. The fiber mesh may be made of elastane, latex, lycra, polyurethane, nylon, nylon coated with other materials such as cotton, composite springs, or other appropriate material. In other embodiments, dimensional surface structures or inflatable sinuses that are encapsulated in the surface substrate of the balloon (30) may be used to produce the textured surface.

Figure 6:
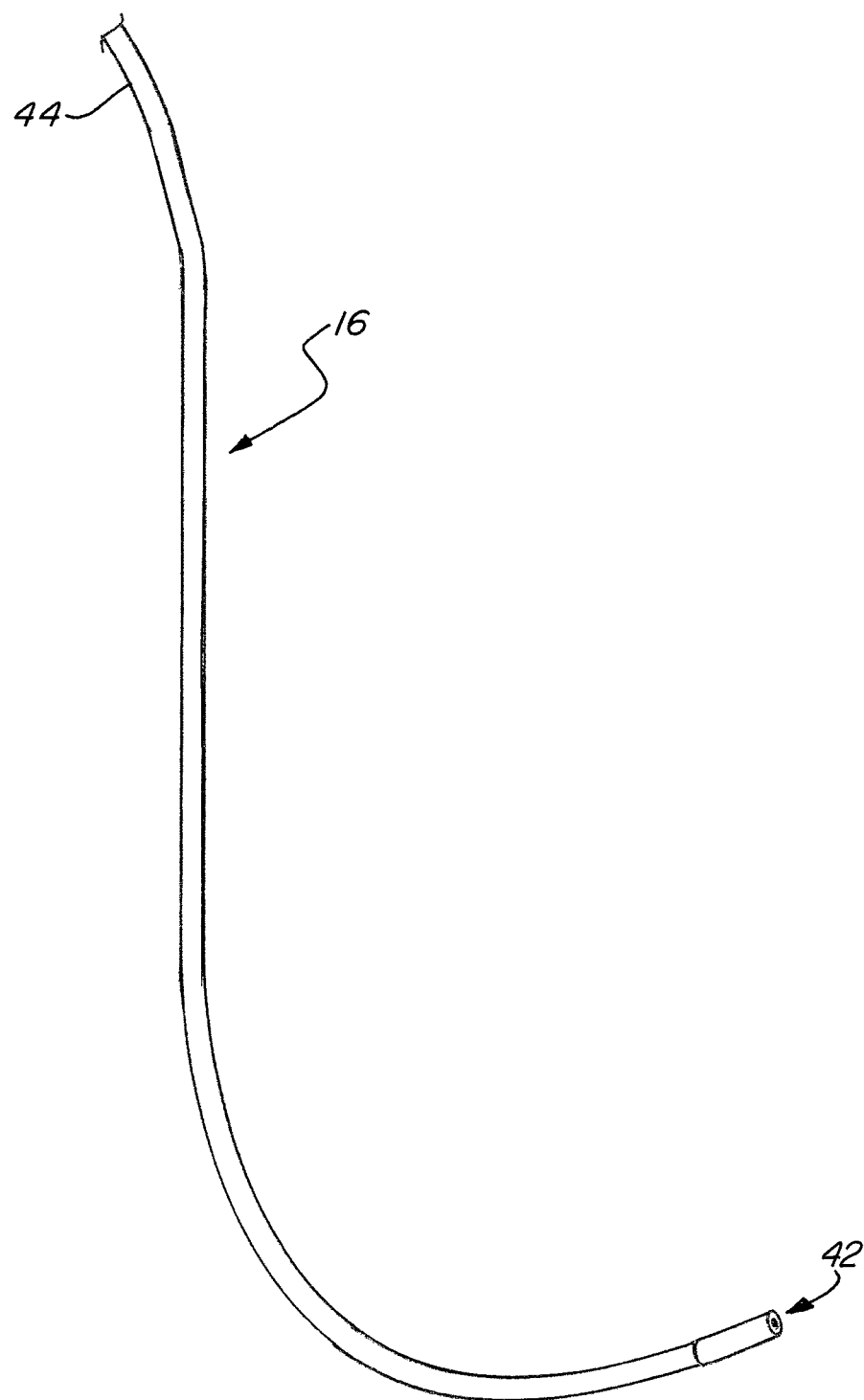
FIG. 6 is a front perspective view of an imaging device of the laryngeal access system of FIG. 1A.

The system (10) further includes an imaging device (16), one exemplary embodiment of which is illustrated in FIG. 6. The imaging device (16) has an elongated shaft with a distal end (42) and a proximal end (44). The shaft is made with any suitable rigid or semi-rigid material that can conform to the shape of the ET tube (14) and/or the laryngeal blade (12). In some embodiments, the imaging device (16) has an articulating distal portion that can be bent to different angles to provide for a better visualization of the surrounding anatomy. Any of the actuating mechanisms described above may be positioned at a proximal end of the imaging device and used to articulate the imaging device.

The imaging device (16) may comprise any imaging device suitable for viewing the target area, such as a coherent fiber bundle or appropriate optical element and lens assembly in conjunction with an imaging sensor (e.g., CMOS, CCD), having a sufficiently small outer diameter, preferably about 0.75 mm-2.5 mm, and more preferably about 1 mm or less.

Figure 7:
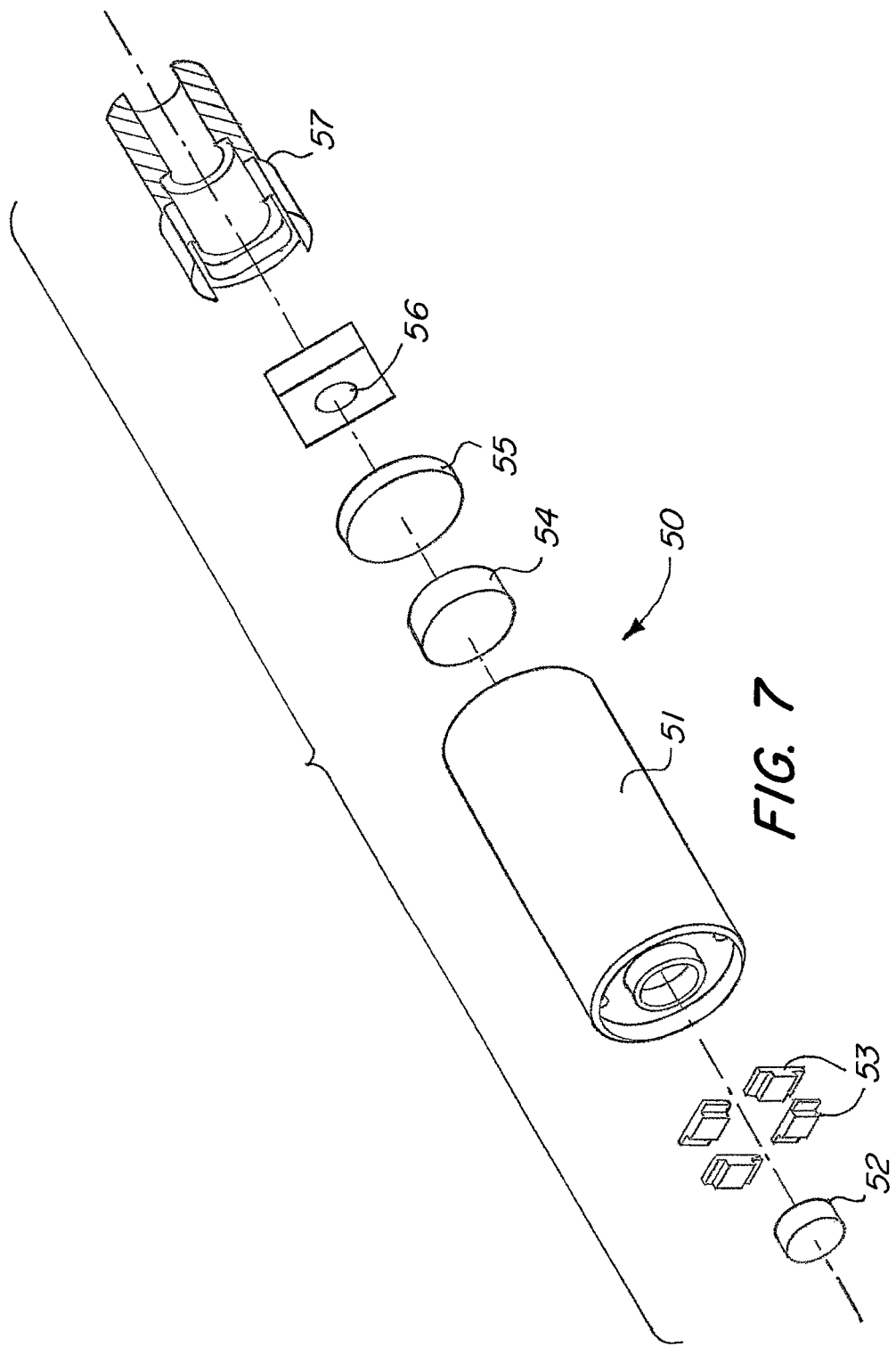
FIG. 7 is an exploded view of the camera of the imaging device of FIG. 6.

In some embodiments, there is a camera head positioned at the distal end (42) of the shaft. The camera head can have any suitable design. One of the exemplary embodiments of the camera head is illustrated in FIG. 7. The camera head (50) includes a camera housing (51) that houses all camera components. The housing (51) is made with any suitable material, such as plastic or metal, and has any desired shape and size. The camera also includes one or more lens positioned in the housing. In the embodiment shown in these figures, the camera includes two plano-convex lenses (54) and (55) positioned opposite of each other such that the convex sides of the lenses are facing each other. It is understood that any other lens type and arrangement may be used in accordance with the present invention, as desired.

The camera head (50) further includes an imaging sensor (56) positioned proximally from the lens (54) and (55). Any type of imaging sensor may be used. The imaging sensor (56) is coupled a sensor mount (57) to fixate the sensor inside the housing. In one advantageous embodiment, a CMOS sensor is used. The housing (51) also has one or more illumination devices (53), e.g. LEDs, lasers, and/or fiber optic cables, positioned distally from the lens. It is understood than other types of illumination devices may be used. Furthermore, illumination devices that are separate from the camera may also be utilized in accordance with the present invention.

The illumination devices emit various types of light, depending on desired application. For example, the illumination devices may emit ambient light, visible spectrum light, ultraviolet light, infrared light, near infrared light, etc. A distal end of the housing (51) has a screen or cover (52) that seals the distal end of the housing to protect the camera components positioned in the housing.

It is understood that the camera design illustrated in the above figures is only exemplary and that any other camera head design may be used with the system of the present invention.

In certain embodiments, the laryngeal access system (10) further includes a storage device (not shown), which is provided to store, for example, the image data captured by the imaging device (16). The storage device may comprise virtually any type of storage device and may be internal or external to the system (10). For example, suitable storage devices include a magnetic, high density hard drive, a writable medium including a CD/DVD, or a card inserted into the screen casing including, for example, a removable drive, such as a thumb drive, volatile or non-volatile memory, etc.

In some embodiments, the laryngeal access system (10) is coupled to a processor for receiving and processing image data captured by the imaging device (16) and/or the imaging device (17) positioned on the blade (12). Any suitable type of a processor may be used. The system (10) is connected to the processor via a cable connection, which may comprise, for example, an optical channel and a data channel. Alternatively, it is understood that the system (10) may be wirelessly coupled to the processor via a network connection. It is contemplated that network connection may comprise, for example, an Internet connection.

The processor may be coupled to a remote storage, which may comprise virtually any type of memory device, as described above. Additionally, virtually any type of digital data may be saved on remote storage, such as, but not limited to, configuration data, update information, image data, etc. The processor is further connected to a display via a cable or wireless connection, for displaying the processed image data to the user. The display may be any suitable type of display, such as a computer monitor or a television screen.

It is noted, however, that in some embodiments, the image data generated by the imaging device (16) or (17) may also be processed by a control device positioned on the blade (12). In such embodiments, the processed image data may then be transmitted from the control device to the processor via cable or wirelessly. The processor is then used to further process the information and/or transmit the image data to the display.

The connection coupling the laryngeal access system (10) to the processor (10) can include a two-way communication. For example, in addition to the imaging data captured by the imaging device (16) or (17), the system (10) may transmit other information, such as, for example, identification/use/maintenance data, to the processor. The processor may then use this information to automatically configure to function properly with the system (10). Additionally, command and control data may be transmitted to the system (10) from the processor, which may include commands for moving the imaging device (16) or articulating the blade (12). In such embodiments, an input device, such as keyboard, mouse, track pad, microphone, etc., may be coupled to the processor and used by a user to provide input commands for the system (10). It is further contemplated that, rather than having a separate input device, the display may be provided as a touch screen control device, which may be used to both display image data and provide for control/command inputs.

The laryngeal access system (10) may include a power cable for providing electrical power to the electronics and illuminating devices, or electrical power may be provided via battery power (such as a rechargeable battery) positioned on the blade (12) or removably connected to the blade. Alternatively, it is contemplated that the system (10) may be wirelessly powered via any known coupling devices.

In additional embodiments, the imaging device (16) is in a form of an imaging stylet, such as described in the U.S. Publication No. 2014/0275778 to Gunday et al., the disclosure of which is incorporated herein in its entirety, and illustrated in FIGS. 8A and 8B.

The imaging stylet (60) includes an outer housing (62) and an opening (64) provided at a distal end of the housing. The outer housing (62) is made of any suitable malleable material, such as polyether block amide material (Pebax®), which preferably has a low modulus of elasticity with minimized resistance to bending. The outer diameter of the outer housing (62) should usually be made as small as possible. Typically, the outer diameter is less than about 5 mm. Preferably, the outer diameter of the catheter body is less than 3 mm.

In some embodiments, the outer housing (62) is an extruded cylindrical member having at least three inner lumens that accommodate various components of the imaging stylet (60), as described in more detail below. It is understood, however, that any other suitable structure/configuration of the outer housing (62) may be utilized in accordance with the present invention.

The imaging stylet (60) also includes a support member (66) disposed within the outer housing (62). The support member (66) is preferably a solid rod having a cup-shaped portion at its distal end. The support member (66) is constructed with any suitable malleable semi-rigid material, such as aluminum, that is capable of being bent to a certain shape and also being capable of retaining that bent shape. Before use, the support member (66) is first bent to a certain angulation that corresponds to a shape of larynx and trachea of a particular patient being intubated. The support member provides rigidity to the flexible outer housing to facilitate the intubation process.

An imaging device (68) is further disposed in the outer housing (62), preferably via an imaging device lumen. The imaging device includes an imaging device head (76) positioned adjacent the opening (64) at the distal end (78) of the outer housing (62). Any suitable type of imaging device may be used in accordance with the present invention. In one exemplary embodiment, the imaging device (68) is a camera provided with a fiber optic image bundle (74) introduced through the imaging device lumen of the outer housing via a port provided at the proximal end to image the surrounding area. The fiber optic image bundle may be made of coherent imaging fibers at the core, and a lens provided at the distal end of the camera head. The camera may incorporate various types of object lenses at the distal tip for different fields of view (i.e. 50°, 130°, etc.) and various depths of field. At the proximal end of the fiber optic bundle, the coherent imaging fibers may be interfaced to any suitable type of digital imaging device, including, but not limited to, a CMOS device or a CCD.

In some advantageous embodiments, the imaging device (68) further includes at least one illumination device for illuminating surrounding tissue during the intubation process. For example, the imaging device may include one or more light emitting diodes positioned around the camera lens. It should be noted, however, that other sources of illumination may also be employed. For example, in other embodiments, two separate bundles, one for illumination and the other for image can also be used. Similarly to the cohered fibers, the illumination fibers are interfaced to a light source. It should also be noted that the image sensor can be located at the distal end of the imaging device head, eliminating the need for a coherent imaging fiber bundle, thus increasing the image quality and reducing cost.

The imaging device head (76) is attached to a distal end of the support member (66) by a resilient member (70). The resilient member (70) is made with any type of suitable material that returns to its original form after being deformed. In one advantageous embodiment, the resilient member (70) is a leaf-spring.

The imaging device head (76) is further connected to an actuator (72) disposed in an actuation lumen of the outer housing (62). The actuator (72) may be a push/pull wire, a distal end of which is connected to the imaging device head (76) and a proximal end of which is coupled to a control device provided at the proximal end of the outer housing (62).

In its inactivated position, the imaging device head (76) is aligned with the longitudinal axis of the distal end (78) of the outer housing (62) such that it lays flat on the cup-shaped distal portion of the support member (66). When the push/pull wire (72) is pulled by the user via the control device, the imaging device head (76) is brought from its inactivated position to an activated position, wherein it extends out of the opening (64) in the outer housing (62) at a certain angle relative to the longitudinal axis of the housing, as shown in the figure above. The angle at which the imaging device (76) extends out of the outer housing (62) may be adjusted as desired to facilitate viewing of the patient's larynx and trachea anatomy during the intubation process to ensure that the patient's vocal cords or other internal structures are not damaged. In some advantageous embodiments, the angle is in the range of from about five degrees to about forty degrees. If desired, the imaging stylet (60) can also be rotated via the control device such that other sides of the patient's airway passage may be viewed as well. Thereby, the intubation system of the present invention allows for a complete 360 degree visualization of the airway passage anatomy. It should be noted that any other type of actuation device may also be used to actuate the imaging device (76) in accordance with the present invention.

Image data collected by the imaging device (16) is transmitted to a processor coupled thereto either wirelessly or via a cable connection. The image data is processed and displayed to the user via a display coupled to the processor.

Referring back to the first figure above, before the intubation procedure is commenced, the imaging device (16) is inserted into the ET tube (14) via the port (24). The ET tube (14) is then slid into the laryngeal blade (12) via the side-loading channel (22) such that the imaging device head is positioned at the distal end of the blade (12) and the proximal section of the ET tube (14) extends out of the opening (28) at the proximal end of the blade (12). The blade is then inserted into a patient's mouth. The blade actuator portion (20) is grasped by the physician and the blade is advanced into the person's trachea, while the distal deflecting portion (18) of the blade is actuated to conform to the person's anatomy and facilitate atraumatic insertion of the blade. At the same time, the imaging device (16) is used to provide illumination and visualization of the tracheal anatomy to further facilitate the insertion process. All of this may be accomplished via a one-hand approach.

Once the blade (12) is positioned at the desired site inside the person's trachea, the blade is slid off the ET tube (14) via the side-loading channel (22) and is withdrawn from the person's trachea and throat. The balloon (30) on the tube (14) is inflated via the fluid source (26) such that it grips the surrounding tissue to fixate the ET tube (14) inside the person's trachea. The imaging device (16) may then be withdrawn from the ET tube (14) and the tube is connected to a respiratory device to assist the person's breathing.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention.

What is claimed is:

1. A laryngeal access system, comprising:
   a laryngeal blade with a proximal portion and a distal portion;
   an inner channel extending longitudinally through the laryngeal blade;
   wherein the laryngeal blade has a circumferential wall extending from the proximal portion to the distal portion of the blade, the circumferential wall defining the inner channel, and wherein the laryngeal blade has a side-loading channel extending along an entire length of the circumferential wall from a proximal end of the blade to a distal end of the blade such that an object can pass through the circumferential wall via the side-loading channel into the inner channel;
   wherein an inner wall of the blade comprises at least one protrusion extending into the inner channel and configured to movably grip an object positioned in the inner channel;
   an articulating member provided at the distal portion of the blade; and an actuator provided at the proximal portion of the blade and coupled to the articulating member, wherein the actuator moves the articulating member from a first position, in which the articulating member has a first longitudinal axis, to a second position, in which the articulating member extends at an angle relative to the first longitudinal axis.

2. The laryngeal access system of claim 1, wherein the actuator is capable of moving the articulating member from the first position to the second position in response to application of pressure.

3. The laryngeal access system of claim 1, wherein the actuator is capable of moving the articulating member in response to linear displacement of the actuator.

4. The laryngeal access system of claim 1, wherein the actuator is capable of moving the articulating member in response to rotational movement of the actuator.

5. The laryngeal access system of claim 1, wherein the actuator is coupled to the articulating member via a wire.

6. The laryngeal access system of claim 1, further comprising an imaging device movably disposed in the inner channel.

7. The laryngeal access system of claim 6, wherein said imaging device comprises at least one of a CMOS device and a CCD device.

8. The laryngeal access system of claim 6, wherein said imaging device comprises at least one illumination device generating light for illuminating surrounding tissue.

9. The laryngeal access system of claim 1, wherein a portion of the laryngeal blade proximal to the distal end of the blade is substantially flexible such that it bends when the articulating member is moved to a second position.

10. The laryngeal access system of claim 1, wherein at least a portion of the laryngeal blade is substantially transparent to allow for imaging of surrounding tissue through the blade.

11. The laryngeal access system of claim 1, wherein the articulating member comprises an imaging device disposed thereon.

12. The laryngeal access system of claim 11, wherein the articulating member further comprises an illumination device positioned adjacent the imaging device.

13. The laryngeal access system of claim 1, wherein the laryngeal blade comprises at least one sensor positioned thereon.

14. The laryngeal access system of claim 13, wherein the at least one sensor comprises at least one of a pulse oximetry sensor, a blood pressure sensor, a temperature sensor, a flow sensor and a biofilm sensor.

15. The laryngeal access system of claim 1, further comprising an endotracheal tube removably accommodated in the inner channel via the side-mounted channel and having a lumen.

16. The laryngeal access system of claim 15, wherein the endotracheal tube comprises an inflatable balloon positioned adjacent a distal end of the endotracheal tube.

17. The laryngeal access system of claim 16, further comprising a fluid source coupled to the inflatable balloon via an inflation lumen provided in the endotracheal tube.

* * * * *